(12) United States Patent
Bonner et al.

(10) Patent No.: US 9,504,820 B2
(45) Date of Patent: Nov. 29, 2016

(54) SYSTEM AND METHOD FOR IMPLANTATION OF AN IMPLANTABLE MEDICAL DEVICE

(75) Inventors: Matthew D. Bonner, Plymouth, MN (US); Raymond W. Usher, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 1295 days.

(21) Appl. No.: 12/915,859

(22) Filed: Oct. 29, 2010

(65) Prior Publication Data
US 2012/0109149 A1 May 3, 2012

(51) Int. Cl.
*A61B 19/00* (2006.01)
*A61N 1/05* (2006.01)
*A61N 1/372* (2006.01)
*A61N 1/375* (2006.01)

(52) U.S. Cl.
CPC .............. *A61N 1/057* (2013.01); *A61N 1/372* (2013.01); *A61N 1/3756* (2013.01); *A61N 1/37205* (2013.01); *A61N 2001/058* (2013.01); *A61N 2001/0578* (2013.01)

(58) Field of Classification Search
CPC .. A61N 1/057; A61N 1/372; A61N 1/37205; A61N 1/3756; A61N 2001/0578; A61N 2001/058
USPC ............................................ 606/129; 607/36
See application file for complete search history.

(56) References Cited

U.S. PATENT DOCUMENTS

| 5,697,936 | A * | 12/1997 | Shipko et al. ................. 606/108 |
| 6,370,434 | B1 | 4/2002 | Zhang et al. |
| 7,780,650 | B2 * | 8/2010 | Frassica et al. ............... 604/544 |
| 7,840,281 | B2 * | 11/2010 | Kveen et al. .................. 607/126 |
| 2004/0176797 | A1 * | 9/2004 | Opolski .......................... 606/213 |
| 2005/0033394 | A1 | 2/2005 | Seifert et al. |
| 2006/0247753 | A1 | 11/2006 | Wenger |
| 2006/0271109 | A1 | 11/2006 | Kuzma |
| 2009/0082828 | A1 * | 3/2009 | Ostroff ............................. 607/36 |
| 2009/0093822 | A1 * | 4/2009 | Ducharme .................... 606/108 |

FOREIGN PATENT DOCUMENTS

WO 2009/039400 A1 3/2009

OTHER PUBLICATIONS (PCT/US2011/056875) PCT Notification of Transmittal of the International Search Report and the Written Opinion of the International Searching Authority.
(PCT/US2011/056885) PCT Notification of Transmittal of the International Search Report and the Written Opinion of the International Searching Authority.

* cited by examiner

*Primary Examiner* — Diane Yabut
*Assistant Examiner* — Martin T Ton
(74) *Attorney, Agent, or Firm* — Evans M. Mburu (57) ABSTRACT

System and method for implanting an implantable medical device. A catheter has a lumen and a distal portion configured for insertion in proximity of tissue of a patient. An implantable medical device has a fixation member operatively coupled to the housing having an unengaged state when in the lumen of the catheter and an engaged state configured to engage tissue of a patient when outside of the lumen of the catheter, the medical device being magnetically attractable. A magnetic element is configured to magnetically engage the implantable medical device and to pass through the lumen of the catheter.

16 Claims, 7 Drawing Sheets

SYSTEM AND METHOD FOR IMPLANTATION OF AN IMPLANTABLE MEDICAL DEVICE

FIELD

The present invention relates generally to devices to implant implantable medical devices from a patient and, in particular, to such devices to implant implantable medical devices.

BACKGROUND

Electrically active implantable medical devices such as pacemakers and cardioverter/defibrillators are well known in the art. Such implantable medical devices commonly and historically have been configured to be implanted within the patient some distance away from the heart of the patient. Pacemakers have traditionally been positioned in the musculature or other tissue of the patient's shoulder below the collar bone. Cardioverter/defibrillators are typically implanted either in the patient's side or, with recent advances in miniaturization, in the patient's shoulder. By utilizing transvenous leads to position electrodes within and in proximity of the heart, such implantable medical devices may be so positioned away from the heart and still be configured to treat cardiac conditions.

Because such implantable medical devices are positioned in the patient's shoulder or other relatively accessible location in the patient's body, implantation and explantation of such implantable medical devices may be relatively straight forward. In particular, because such implantable medical devices are both implanted at a relatively shallow depth and are of a size which is relatively easily manipulable for a medical professional, such implantable medical devices have not commonly required specialized tools for removal from the patient. Such devices may be relatively straightforwardly implanted in the patient by accessing the implantation location surgically, securing the device in the hands, placing the device in the implantation location, connecting the implantable medical device to the transvenous leads and surgically closing the implantation location.

Recently, however, miniaturization of implantable cardiac devices, particularly pacemakers, has allowed devices to be manufactured of a size small enough to permit implantation of the device within the heart of the patient or within other organs or parts of the body with similar space constraints, such as the epicardium, the pericardium, the lungs and the peripheral vascular system. Such developments may reduce the discomfort a patient may experience having an implantable medical device implanted at a relatively shallow depth in their shoulder and obviate the need for invasive transvenous leads. Pacemakers with these qualities may be referred to as leadless pacemakers. However, while the musculature and tissue of the shoulder may provide relatively easy physical access to a leadless pacemaker or other leadless implantable medical device, inserting and positioning the leadless pacemaker in the heart of the patient may make the leadless pacemaker considerably more challenging to physically access for implantation from the patient relative to a device positioned in the patient's shoulder.

SUMMARY

Because implantable medical devices implanted in the heart need to be fixed to some extent within the heart, the location within the heart at which implantable medical device is desirously implanted will tend to move with the beating and other movement of the heart. Moreover, the vasculature of the patient presents a relatively constricted conduit to access the heart. Thus, physically manipulating the implantable medical device for insertion may be challenging. In addition, merely putting the implantable medical device in proximity of the desired location may not result in the implantable medical device being secured to the desired location.

An implantable medical device implantation and extraction system has been developed to address these challenges. A catheter with a longitudinal lumen has been configured to be passed through the vasculature of the patient and placed in proximity of the implant location within the heart of the patient. An implantable medical device is configured to be seated within the lumen of the catheter. A magnetic element is configured to pass through the lumen of the catheter and contact the implantable medical device. A magnet on the magnetic element is configured to magnetically attract and secure the implantable medical device. After the catheter is positioned proximate the implantation location the magnetic element may be utilized to eject the implantable device and secure the implantable medical device to the implantation location.

In an embodiment, a medical device system has a catheter, an implantable medical device and a magnetic element. The catheter has a lumen and a distal portion configured for insertion in proximity of tissue of a patient. The implantable medical device has a fixation member operatively coupled to the housing having an unengaged state when in the lumen of the catheter and an engaged state configured to engage tissue of a patient when outside of the lumen of the catheter, the medical device being magnetically attractable. The magnetic element is configured to magnetically engage the implantable medical device and to pass through the lumen of the catheter.

In an embodiment, the magnetic element is configured to convert the fixation member of the implantable medical device from the unengaged state to the engaged state to engage the tissue of the patient In an embodiment, the magnetic attraction between the magnetic element and the implantable medical device is at least one quarter Newtons.

In an embodiment, the fixation member comprises at least one tine having a fixation force configured to secure the at least one tine to the tissue of the patient.

In an embodiment, the magnetic attraction between the magnetic element and the implantable medical device is less than the fixation force of the at least one tine.

In an embodiment, the fixation member has an engaged state engaged with the tissue of the patient while implanted and an unengaged state unengaged with the tissue of the patient and wherein the fixation member changes from the unengaged state to the engaged state by operation of the magnetic element.

In an embodiment, the fixation member is located proximate a distal portion of the implantable medical device.

In an embodiment, a proximal portion of the implantable medical device is magnetically attractable to the magnetic element.

In an embodiment, the system further has a snare having a distal portion and configured for insertion, the snare having a mechanical engaging member proximate the distal portion of the snare, the snare being configured to pass through the catheter and mechanically engage the implantable medical device.

In an embodiment, the snare is configured to pass through the catheter and mechanically engage the implantable medical device while the magnetic element has magnetically engaged the implantable medical device.

In an embodiment, when the magnetic element is magnetically engaged with the implantable medical device, the magnetic element provides, at least in part, a physical guide for the snare to mechanically engage the implantable medical device.

In an embodiment, the fixation member comprises at least one tine having a fixation force securing the at least one tine to the tissue of the patient and wherein the mechanical engaging member mechanically engages the implantable medical device proximate the second portion of the implantable medical device with a connection force greater than the fixation force of the at least one tine.

In an embodiment, the mechanical engaging member has a lasso.

In an embodiment, the fixation member is located proximate a first end of the implantable medical device and wherein the implantable medical device further comprises a magnetic component positioned proximate a second end of the implantable medical device opposite the first end providing the magnetic attraction.

In an embodiment, the magnetic component of the implantable medical device comprises a magnet.

In an embodiment, the catheter is configured to be inserted transvenously.

In an embodiment, a method of implanting a magnetically attractable implantable medical device having a fixation member operatively coupled to a housing is disclosed, the fixation member having an engaged state configured to engage tissue of a patient and an unengaged state. A catheter having a lumen and a distal portion is inserted in proximity of the tissue of the patient. The implantable medical device is inserted into the lumen of the catheter, the fixation member being in the unengaged state. A magnetic element is inserted into the lumen of the catheter. The implantable medical device is magnetically engaged with a magnetic attraction from the magnetic element. Then, the implantable medical device is ejected from the lumen of the catheter causing the fixation member to engage the tissue of the patient in the engaged state. The magnetic element is disengaged from the implantable medical device. Then, the catheter and the magnetic element are withdrawn from the patient leaving the implantable medical device engaged with the tissue of the patient.

In an embodiment, the method has the further step, after the engaging step and before the disengaging step, of exerting a retracting force on the implantable medical device with the magnetic element less than the fixation force to verify the fixation member has engaged the tissue with a force at least as great as the magnetic attraction between the magnetic element and the implantable medical device.

In an embodiment, the ejecting the implantable medical device from the lumen of the catheter step is performed by applying a longitudinal force on the implantable medical device with the magnetic element.

In an embodiment, the inserting the catheter step and the withdrawing step are transvenous.

DESCRIPTION

Figure 1:
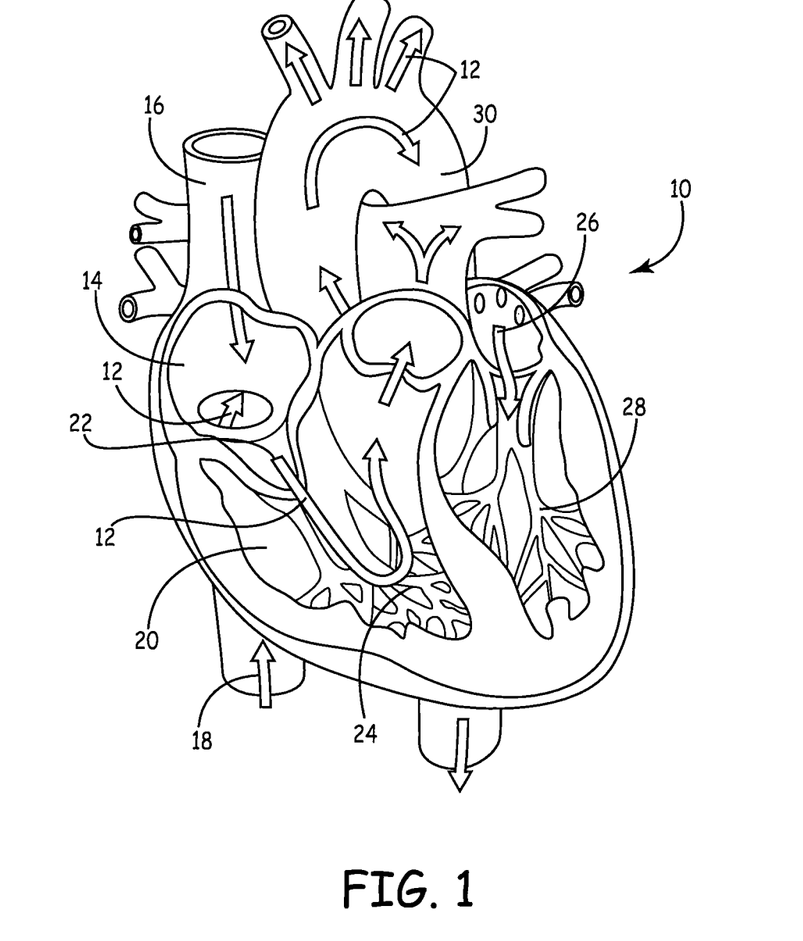
FIG. 1 is a partial cross-sectional depiction of a human heart.

FIG. 1 is a cutaway depiction of human heart 10. Arrows 12 illustrate the flow of blood through heart 10. Right atrium 14 is accessed by superior vena cava 16 and inferior vena cava 18. Blood flows from right atrium 14 to right ventricle 20 through tricuspid valve 22. Chordae tendineae 24 in right ventricle 20 act to keep tricuspid valve 22 closed during the contraction of the right ventricle 20. After blood flows from right ventricle 20 to the lungs (not pictured), the blood flows back to left atrium 26 and then into left ventricle 28. From left ventricle 28 blood flows to the body via aorta 30.

Figure 2:
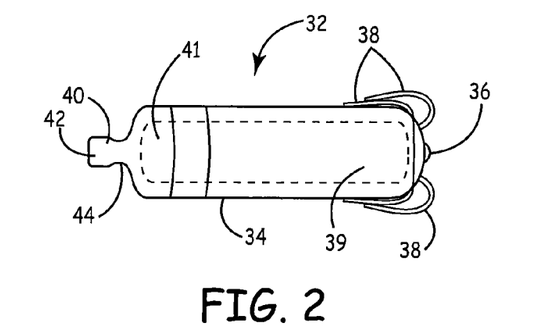
FIG. 2 illustrates a leadless pacemaker.

FIG. 2 shows leadless pacemaker 32 which is configured to be transvenously implantable within heart 10. Leadless pacemaker 32 may be further or alternatively be configured to be inserted non-tranvenously, variably into heart 10, in the epicardium or pericardium, in proximity of heart 10, within the patient's peripheral vascular system, lungs or elsewhere within the patient. Leadless pacemaker 32 may incorporate various internal componentry (not illustrated) common to implantable pacemakers known in the art, including a controller, a power source, sensors, therapy circuitry, telemetry circuitry and other electronics useful for operating leadless pacemaker. Implantable medical devices such as cardioverter/defibrillators configured to be leadless implantable medical devices may be substituted for leadless pacemaker 32.

As illustrated, housing 34 is generally cylindrical, though alternative configurations are also envisioned. In various embodiments, housing 34 is made of non-corrosive materials. In an embodiment, housing 34 is made of titanium. In alternative embodiments, housing 34 is made of ferrous or other magnetically attractive materials. In such embodiments, housing 34 may be covered in a non-bioreactive or non-corrosive material to make leadless pacemaker 32 safe for implantation in heart 10. Electrode 36 is configured to deliver pacing energy generated by the therapy circuitry and the internal power source to heart 10. Additional electrodes 36 may be positioned as needed on housing 34 to deliver a therapeutic output to heart 10.

One or more tines 38 create a fixation member and are configured to engage tissue in heart 10 to secure leadless pacemaker 32 within heart 10. In various embodiments, alternative fixation members may be applied as known in the art, including screws and helixes. In the illustrated embodiment, tines 38 are positioned proximate first end 39 of leadless pacemaker 32. In various embodiments, tines 38 are configured to ensnare chordae tendineae 24 within right ventricle 20, securing leadless pacemaker 32 within heart 10. Alternatively, tines 38 may engage cardiac tissue in or around tricuspid valve 22, left ventricle 28 or elsewhere in heart 10. In further alternative embodiments, tines 38 may engage tissue in the epicardial space, lung and vasculature. When engaged with chordae tendineae 24 or any patient tissue, tines 38 exert a fixation force which maintains leadless pacemaker 32 within heart 10. In various embodiments, tines 38 are made from material which is flexible to achieve multiple positions but resiliently biased in a configuration which allows tines 38 to be ensnared in chordae tendineae 24 or other tissue of heart 10. In various embodiments, tines 38 are formed from a shape memory alloy. In an embodiment, tines 38 are formed from Nitinol.

Projection 40, e.g., a post, incorporates magnet 42 and indentation 44. As illustrated, projection 40 is generally cylindrical and positioned proximate second end 41 of leadless pacemaker 32. In alternative embodiments, projection 40, along with indentation 44, are alternatively shaped to facilitate a mechanical or connection force with an implantable medical device system discussed in detail below. In alternative embodiments, indentation 44 is not incorporated in projection 40. In alternative embodiments, projection 40 is not incorporated in leadless pacemaker 32. In such embodiments, magnet 42 is incorporated into housing 34. In further alternative embodiments where housing 34 is ferrous or which otherwise creates a magnetic attraction with a magnet, magnet 42 is not incorporated. Alternatively, magnet 42 is substituted with a magnetic component which is attracted to a magnet but which is not itself a magnet. In various such embodiments, projection 40 and indentation 44 are incorporated in leadless pacemaker 32. In alternative embodiments, projection 40 and/or indentation 44 are not incorporated in leadless pacemaker 32.

Figure 3:
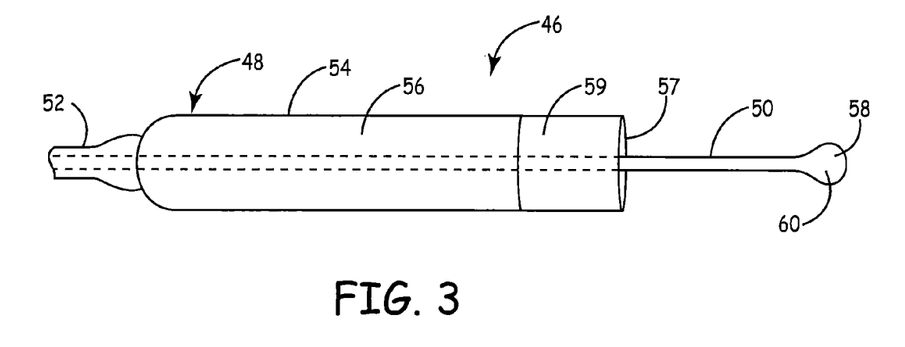
FIG. 3 illustrates an implantable medical device implantation and extraction system.

FIG. 3 is a cutaway view of implantable medical device implantation and extraction system 46. Implantation and extraction system 46 incorporates catheter 48 and magnetic element 50. As illustrated, catheter 48 incorporates body catheter 52 and fairing 54, both of which incorporate a continuous lumen 56 extending the length of catheter 48. Lumen 56 is sized to contain at least element 50 and to allow element 50 to move longitudinally within lumen 56 and project out of opening 57 at distal end 59. As illustrated, fairing 54 is sized and configured to admit and contain leadless pacemaker 32 within lumen 56 so that tines 38 may not engage tissue of heart 10 or of a patient's vasculature. In various alternative embodiments, catheter incorporates body catheter 52 and not fairing 54 as a separate component. In such embodiments, lumen 56 in body catheter 52 may be large enough to admit leadless pacemaker 32. In embodiments incorporating fairing 56, lumen in body catheter 52 may not be large enough to admit leadless pacemaker 32, limiting leadless pacemaker 32 to being positioned in fairing 54.

Catheter 48 is sized to pass through superior vena cava 16 or inferior vena cava 18 and right atrium 14 and into right ventricle 20. In an embodiment, catheter 48 is approximately one hundred twenty (120) centimeters long and a maximum external diameter at fairing 54 of 0.73 centimeters. In an embodiment, lumen 56 has a width of 0.20 centimeters along body catheter 52 and 0.68 centimeters within fairing 54. In various embodiments, catheter 48 is made from materials including, but not limited to, polytetrafluoroethylene, polyether block amide, stainless steel and tungsten.

Element 50 is configured to secure leadless pacemaker 32 using magnet 58 positioned on distal tip 60 of element 50. In various embodiments, magnet 58 is made from neodymium, iron and boron. Alternatively, magnet 58 is made from any material which may be developed to create a magnetic attraction with magnet 42 of leadless pacemaker 32 sufficient to secure leadless pacemaker 32 to element 50. In an embodiment, magnet 58 is an electromagnet. In embodiments where leadless pacemaker 32 does not incorporate magnet 42, magnet 58 of element 50 is strong enough to engage the magnetic material of leadless pacemaker 32 to element 50.

In various embodiments, magnet 58 is a bar magnet or elongate magnet with opposing poles. In various such embodiments, magnet 42 of leadless pacemaker 32 is also a bar magnet or elongate magnet with opposing poles. Where both magnet 42 and magnet 58 are bar or elongate magnets, magnets 42 and 58 may be rotationally fixed with respect to one another when magnetically engaged. In alternative embodiments, magnets 42 and 58 are not bar magnets but are sufficiently strong as to prevent rotation with respect to one another when magnetically engaged. In such embodiments, element 50 may be utilized to rotate leadless pacemaker 32, for instance, when tines 38 or an alternative fixation member such as a screw or helix, may be secured to, or disengaged from cardiac tissue through rotation.

As illustrated, for explantation element 50 has magnet 58 strong enough to engage leadless pacemaker 32 with a magnetic force stronger than the fixation force between tines 38 and chordae tendineae 24. For implantation, element 50 has magnet 58 weak enough to disengage magnet 58 from leadless pacemaker 32 without disengaging leadless pacemaker 32 from cardiac tissue. In various embodiments, each tine 38 creates a fixation force of approximately one Newton. In embodiments with four tines 38, then, for implantation magnet 58 creates less magnetic attraction with leadless pacemaker 32 than one-quarter (¼) Newtons, while for explantation magnet 58 creates greater than four (4) Newtons of magnetic attraction with leadless pacemaker 32.

Figure 4:
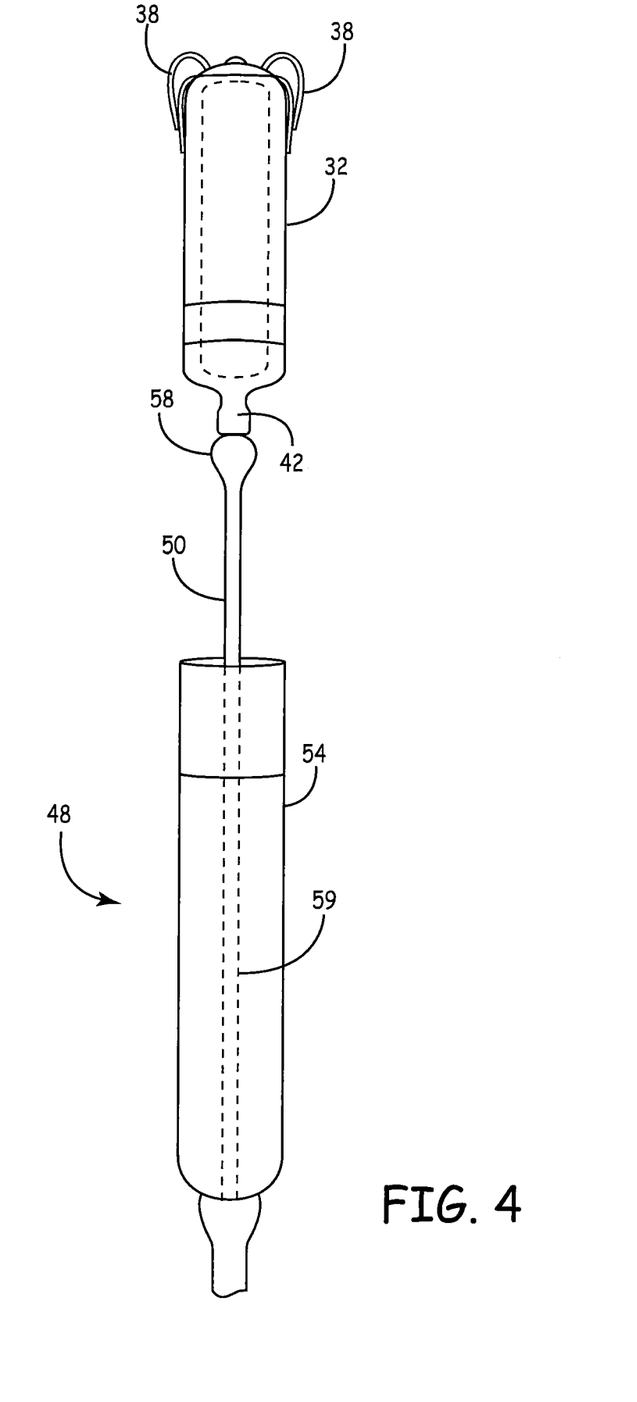
FIG. 4 is the device implantation and extraction system of FIG. 3 engaged with the leadless pacemaker of FIG. 2.

FIG. 4 illustrates magnet 58 of element 50 having established a magnetic force with magnet 42 of leadless pacemaker 32. By establishing a stronger magnetic force than the fixation force, system 46 may act to extract leadless pacemaker 32 from heart 10. By applying the magnetic force between magnet 58 of element 50 and magnet 42 of leadless pacemaker 32 and then pulling on or otherwise exerting a longitudinal force on element 50 which may exert a force on leadless pacemaker 32 which tends to pull tines 38 out of the cardiac tissue, leadless pacemaker 32 may be freed from being secured to heart 10, upon which leadless pacemaker 32 may be retracted into lumen 56 in fairing 54, rendering tines 38 ineffective to engage heart 10 tissue or the vasculature of the patient. Similarly, by pushing on or otherwise exerting a longitudinal force on element 50, a longitudinal force may be exerted on leadless pacemaker 32 in order to push leadless pacemaker 32 from fairing 54 and allow tines 38 to engage cardiac tissue.

Figure 5:
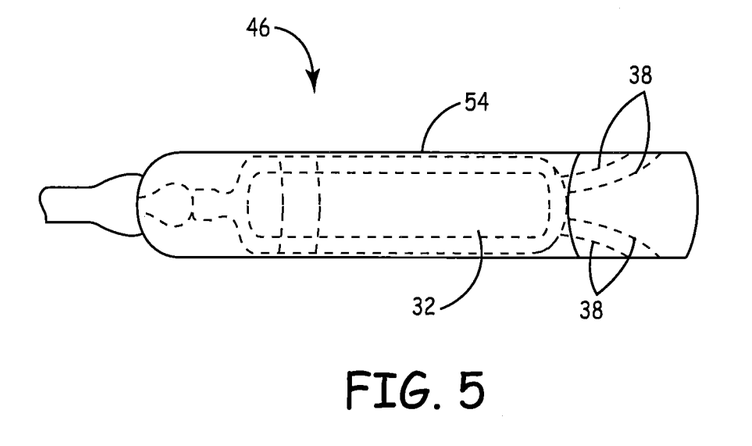
FIG. 5 illustrates the leadless pacemaker of FIG. 2 having been positioned in association with the device implantation and extraction system of FIG. 3.

FIG. 5 is a cutaway illustration of leadless pacemaker 32 having been contained within fairing 54 of system 46. For an implantation procedure, leadless pacemaker 32 may be pre-positioned in fairing 54 prior to be egested near cardiac tissue. For an explantation procedure, leadless pacemaker 32 may have been pulled from engagement with cardiac tissue. During extraction of leadless pacemaker 32, tines 38 tend to move from an implanted state, in which tines 38 are curled to engage cardiac tissue, to an extracted state in which tines 38 are generally straight, allowing tines 38 to be freed from cardiac tissue. Within fairing 54 tines 38 are prevented from engaging with patient tissue, thereby reducing a likelihood of leadless pacemaker 32 from becoming dislodged from system 46. Fairing 54 is sized so that tines 38 remain in the extraction or unengaged state, extending generally straight outward from housing 34, in contrast with tines 38 implanted state, generally curled out from housing 34 so as to engage cardiac tissue.

Figure 6:
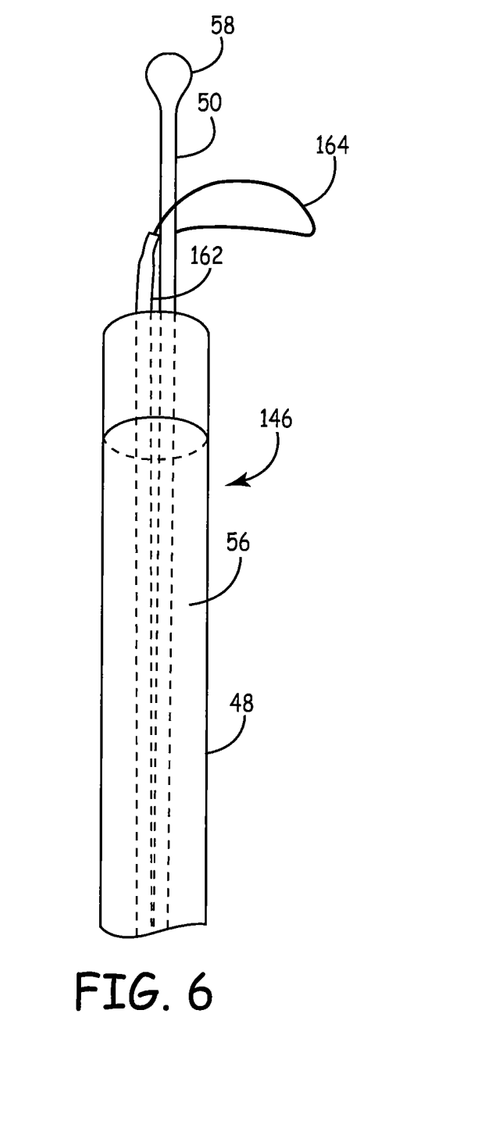
FIG. 6 illustrates an alternative embodiment of a medical device implantation and extraction system.

FIG. 6 is implantable medical device implantation and extraction system 146 incorporating catheter 48, element 50 and snare 162. In the embodiment of system 146, catheter 48 and element 50 are configured to function as described in detail above. However, the magnetic force created between magnet 58 of element 50 and magnet 42 of leadless pacemaker 32 may be supplemented by a mechanical or connection force created by engaging protrusion 40 of leadless pacemaker 32 with a mechanical engaging member such as lasso 164 of snare 162.

In the embodiment of system 146, lumen 56 of catheter 48 is sized to admit and allow to move longitudinally both element 50 and snare 162. In various embodiments, element 50 may provide a guide or rail for snare 162. In an embodiment, element 50 acts as a guide by circumscribing lasso 164 around element 50. As in system 46, element 50 is configured to magnetically engage leadless pacemaker 32 in order to fix leadless pacemaker 32 with respect to system 146. Then snare 162 may be extended through lumen 56 and around protrusion 40.

Figure 7:
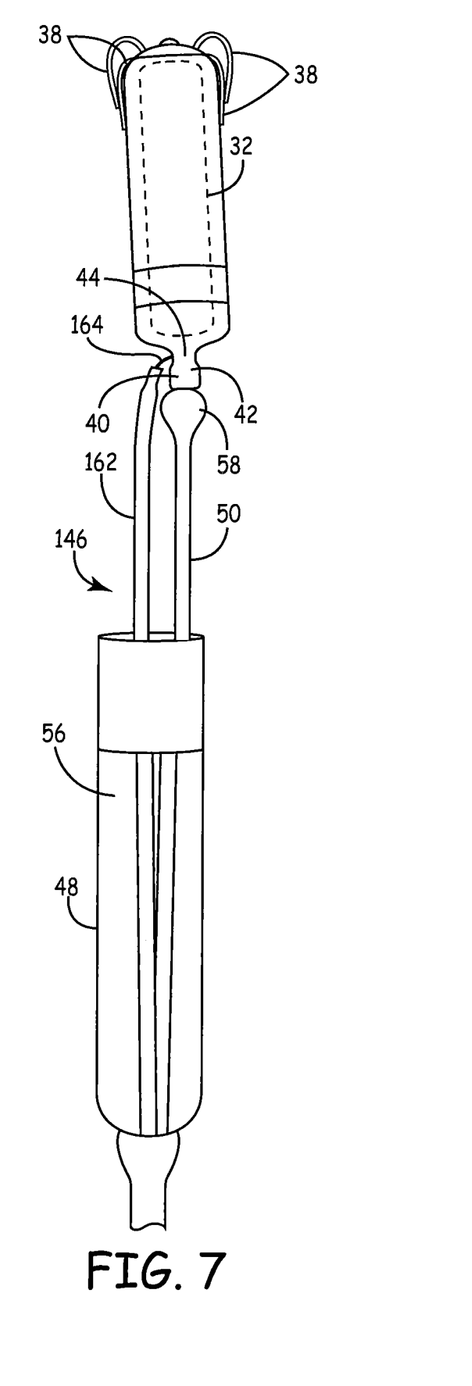
FIG. 7 illustrates the device implantation and extraction system of FIG. 6 engaged with the leadless pacemaker of FIG. 2.

As illustrated in FIG. 7, when positioned around indentation 44 of protrusion 40, lasso 164 may be tightened in order exert a mechanical or connection force on leadless pacemaker 32. Indentation 44 may help provide relatively greater mechanical or connection force on leadless pacemaker 32 than may be attained without indentation 44. Either in combination with the magnetic force exerted by element 50 or without the magnetic force, the mechanical or connection force exerted on protrusion 40 of leadless pacemaker 32 may be greater than the fixation force exerted by tines 38 being engaged with chordae tendineae 24, allowing leadless pacemaker 32 to be extracted from heart 10 in the same manner described above.

In various embodiments of system 146, snare 162 is comprised of the same materials as element 50. In various embodiments, lasso 164 is made from nitinol, stainless steel and gold. Lasso 164 is contractable around projection 40 by manipulating a proximal end of lasso 164 (not pictured) which extends through snare 162 and which is manipulable by a user. By pulling on the proximal end of lasso 162, lasso 162 may be tightened about projection 40 so as to exert the mechanical or connection force on projection 40.

In alternative embodiments in which projection 40 is not incorporated into leadless pacemaker 32, lasso 164 may be tightened about any part of housing 34. In such embodiments, it may be relatively more difficult for lasso 164 to exert a mechanical or connection force than where projection 40 with indentation 44 is provided, though by applying relatively greater force to lasso 164 than may be applied to projection 40 with indentation 44, sufficient mechanical or connection force may be exerted on leadless pacemaker to disengage tines 38 from cardiac tissue.

Figure 8:
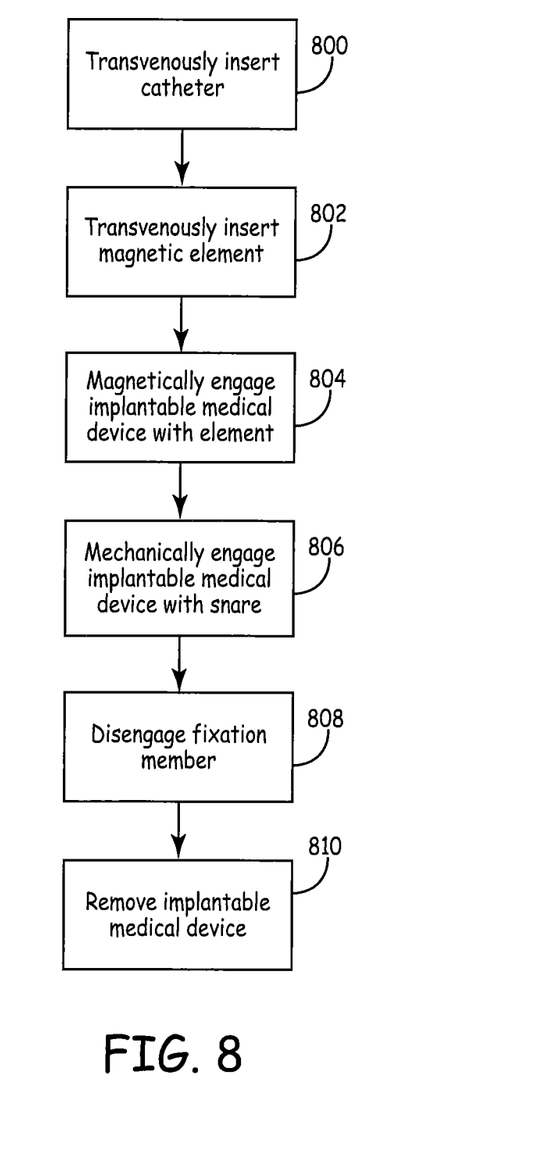
FIG. 8 is a flowchart for utilizing a device extraction system.

FIG. 8 is a flowchart for extracting leadless pacemaker 32 from heart 10 using system 46 or system 146. The flowchart may be readily adapted for utilizing system 46 or system 146 for extracting an implantable medical device from other locations within a patient, such as the lungs or other organs. In various embodiments, the extraction is transvenous. Catheter 48 is inserted (800) into heart 10 and proximate leadless pacemaker 32. Magnetic element 50 is inserted (802) through lumen 56 of catheter 48. In various embodiments, the insertion (800, 802) of catheter 48 and magnetic element 50 occur simultaneously. In one such embodiment, simultaneous insertion occurs by inserting magnetic element 50 into lumen 56 prior to inserting either catheter 48 or magnetic element 50, and then inserting both catheter 48 and magnetic element 50 into the patient at the same time.

Magnet 58 is then used to magnetically engage (804) magnet 42 of leadless pacemaker 32 when element 50 projects through or approaches opening 57 at distal end 59 of catheter. Optionally, and in embodiments incorporating system 146 with snare 162, lasso 164 is utilized to mechanically engage (806) leadless pacemaker 32, in various embodiments projection 40 at indentation 44. Tines 38 are disengaged (808) from cardiac tissue and leadless pacemaker 32 is removed (810) from heart 10 by extracting element 50 and, in embodiments with snare 162, snare 162 through catheter 48. In embodiments with fairing 54, leadless pacemaker 32 is withdrawn into fairing 54 and catheter 48 is removed. In embodiments without fairing 54, element 50 (and optionally snare 162) are removed the length of lumen 56 in order to extract leadless pacemaker 32, whereupon catheter 48 is extracted from the patient.

Figure 9:
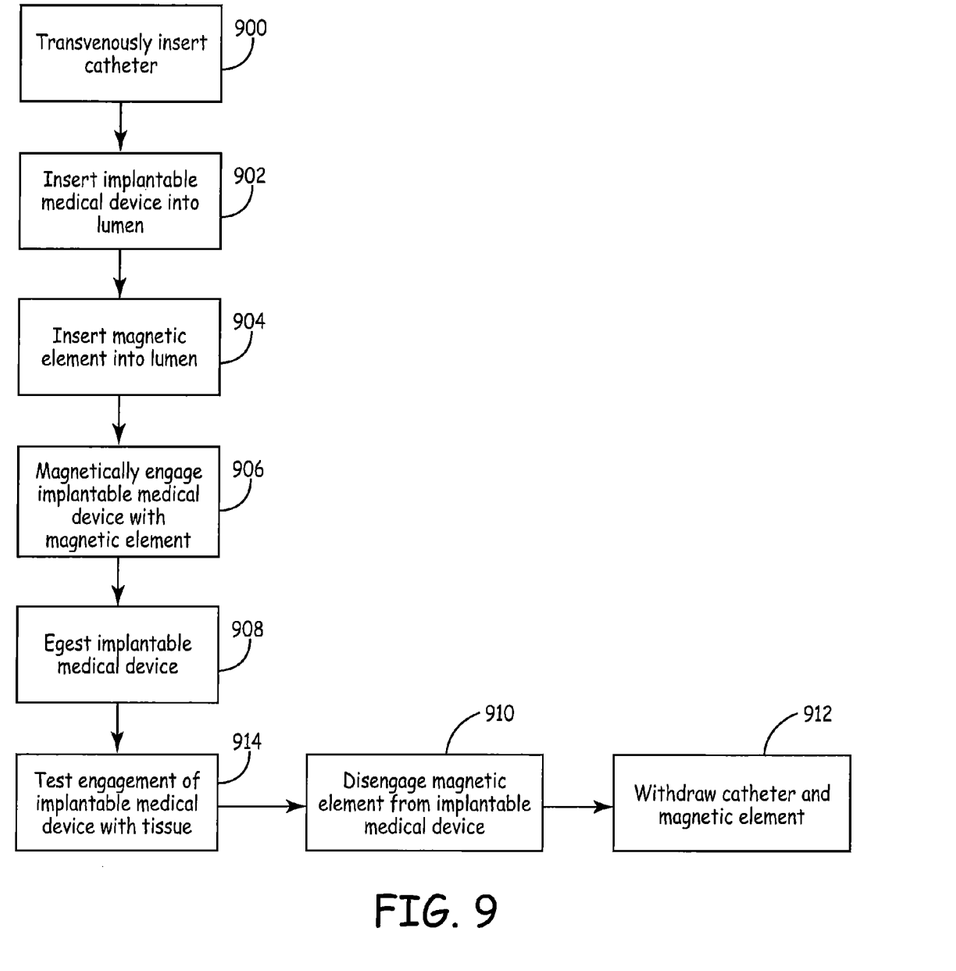
FIG. 9 is a flowchart for utilizing a device implantation system.

FIG. 9 is a flowchart for implanting leadless pacemaker 32 in heart 10 using system 46 or system 146. In various embodiments, implantation is transvenous. Catheter 48 is inserted (900) into heart 10 and proximate patient tissue such as cardiac trabeculae. Leadless pacemaker 32 is inserted (902) into lumen 56 of catheter 48. Variably, leadless pacemaker 32 is inserted into lumen 56 of catheter 48 prior to catheter 48 being inserted into the patient. Alternatively, where lumen 56 is adequately wide over a complete length of catheter 48, catheter 48 may be inserted first and then leadless pacemaker 32 inserted into lumen 56.

Magnetic element 50 is inserted (904) into lumen 56 of catheter 48. In various embodiments, the insertion (900, 904) of catheter 48 and element 50 occur simultaneously. In one such embodiment, simultaneous insertion occurs by inserting element 50 into lumen 56 prior to inserting either catheter 48 or element 50, and then inserting both catheter 48 and element 50 into the patient at the same time. Magnetic element 50 magnetically engages (906) leadless pacemaker 32. The insertion (900) of catheter 48, the insertion (902) of leadless pacemaker 32 into lumen 56, the insertion (904) of magnetic element 50 into lumen 56 and the magnetic engagement (906) of leadless pacemaker 32 with magnetic element 50 may occur in any sequence convenient for use.

Leadless pacemaker 32 is egested (908) from catheter 48, in an embodiment by causing magnetic element 50 to exert a pushing force on leadless pacemaker 32. As leadless pacemaker 32 emerges from catheter 48, tines 38 engage chordae tendineae 24. Magnetic element 50 is disengaged (910) from leadless pacemaker 32, and catheter 48 and magnetic element 50 are withdrawn (912) from the patient, leaving leadless pacemaker 32 engaged with cardiac tissue. Optionally, prior to disengaging (910) magnetic element 50 from leadless pacemaker 32, the engagement of tines 38 with chordae tendineae 24 may be tested (912) by exerting a pulling force on leadless pacemaker 32 less than the magnetic attraction between magnet 58 and leadless pacemaker 32. If tines 38 do not separate from chordae tendineae 24 then leadless pacemaker may be deemed successfully implanted.

Thus, embodiments of the medical device extraction system and method are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A medical device system, comprising:
a catheter having a lumen and a distal portion configured for insertion in proximity of tissue of a patient; and
an implantable medical device having a housing and a fixation member operatively coupled to said housing having an unengaged state when in said lumen of said catheter and an engaged state configured to engage tissue of a patient with a fixation force between said implantable medical device and said tissue of said patient when outside of said lumen of said catheter, said medical device being magnetically attractable; and
a magnetic element being configured to magnetically engage said implantable medical device and to pass through said lumen of said catheter, said magnetic attraction between said magnetic element and said implantable medical device being less than said fixation force engaging said tissue of said patient.

2. The medical device system as in claim 1 wherein said magnetic element is configured to convert said fixation member of said implantable medical device from said unengaged state to said engaged state to engage said tissue of said patient.

3. The medical device system as in claim 2 wherein said magnetic attraction between said magnetic element and said implantable medical device is at least one quarter Newtons.

4. The medical device system as in claim 2 wherein said fixation member comprises at least one tine configured to secure said at least one tine to said tissue of said patient with said fixation force.

5. The medical device system as in claim 4 wherein said magnetic attraction between said magnetic element and said implantable medical device is less than said fixation force of said at least one tine.

6. The medical device system as in claim 1 wherein said fixation member has an engaged state engaged with said tissue of said patient while implanted and an unengaged state unengaged with said tissue of said patient and wherein said fixation member changes from said unengaged state to said engaged state by operation of said magnetic element.

7. The medical device system as in claim 1 wherein said fixation member is located proximate a distal portion of said implantable medical device.

8. The medical device system as in claim 7 wherein a proximal portion of said implantable medical device is magnetically attractable to said magnetic element.

9. The medical device system as in claim 1 further comprising a snare having a distal portion and configured for insertion, said snare having a mechanical engaging member proximate said distal portion of said snare, said snare being configured to pass through said catheter and mechanically engage said implantable medical device.

10. The medical device system as in claim 9 wherein said snare is configured to pass through said catheter and mechanically engage said implantable medical device while said magnetic element has magnetically engaged said implantable medical device.

11. The medical device system as in claim 9 wherein, when said magnetic element is magnetically engaged with said implantable medical device, said magnetic element provides, at least in part, a physical guide for said snare to mechanically engage said implantable medical device.

12. The medical device system as in claim 9 wherein said fixation member comprises at least one tine having a fixation force securing said at least one tine to said tissue of said patient and wherein said mechanical engaging member mechanically engages said implantable medical device proximate said second portion of said implantable medical device with a connection force greater than said fixation force of said at least one tine.

13. The medical device system as in claim 9 wherein said mechanical engaging member comprises a lasso.

14. The medical device system as in claim 1 wherein said fixation member is located proximate a first end of said implantable medical device and wherein said implantable medical device further comprises a magnetic component positioned proximate a second end of said implantable medical device opposite said first end providing said magnetic attraction.

15. The medical device system of claim 14 wherein said magnetic component of said implantable medical device comprises a magnet.

16. The medical device system of claim 1 wherein said catheter is configured to be inserted transvenously.

* * * * *